US012403173B2

(12) United States Patent
Cope et al.

(10) Patent No.: US 12,403,173 B2
(45) Date of Patent: Sep. 2, 2025

(54) MICAFUNGIN COMPOSITIONS

(71) Applicants: BAXTER INTERNATIONAL INC., Deerfield, IL (US); BAXTER HEALTHCARE SA, Glattpark (CH)

(72) Inventors: Sydney J. Cope, Chicago, IL (US); Christine L. Rebbeck, Lake Barrington, IL (US); Mark J. Doty, Grayslake, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 0 days.

(21) Appl. No.: 15/843,634

(22) Filed: Dec. 15, 2017

(65) Prior Publication Data
US 2018/0169180 A1 Jun. 21, 2018

Related U.S. Application Data

(60) Provisional application No. 62/435,695, filed on Dec. 16, 2016.

(51) Int. Cl.
| A61K 38/08 | (2019.01) |
| A61K 9/00 | (2006.01) |
| A61K 9/08 | (2006.01) |
| A61K 31/375 | (2006.01) |
| A61K 47/02 | (2006.01) |
| A61K 47/36 | (2006.01) |
| A61P 31/10 | (2006.01) |

(52) U.S. Cl.
CPC ............ *A61K 38/08* (2013.01); *A61K 9/0019* (2013.01); *A61K 9/08* (2013.01); *A61K 31/375* (2013.01); *A61K 47/02* (2013.01); *A61K 47/36* (2013.01); *A61P 31/10* (2018.01)

(58) Field of Classification Search
CPC ............ A61K 38/08; A61K 9/08; A61P 31/10
See application file for complete search history.

(56) References Cited

U.S. PATENT DOCUMENTS

| 5,849,843 | A | 12/1998 | Laurin et al. |
| 5,998,019 | A | 12/1999 | Rosenbaum et al. |
| 6,107,458 | A | 8/2000 | Ohki et al. |
| 6,265,536 | B1 | 7/2001 | Ohki et al. |
| 6,774,104 | B1 | 8/2004 | Sawai et al. |
| 7,122,565 | B2 | 10/2006 | Vergne et al. |
| 7,198,796 | B2 * | 4/2007 | Stogniew ................. A61P 31/10 514/23 |
| 8,183,233 | B2 | 5/2012 | Kipp et al. |
| 9,115,177 | B2 * | 8/2015 | Jiao ......................... A61P 31/10 |
| 2010/0130450 | A1 | 5/2010 | Lewis et al. |
| 2011/0281788 | A1 | 11/2011 | Coote et al. |
| 2012/0071398 | A1 | 3/2012 | O'Neil |
| 2012/0207762 | A1 | 8/2012 | Kipp et al. |
| 2013/0338060 | A1 * | 12/2013 | Hong ..................... A61K 47/26 514/3.6 |
| 2015/0087583 | A1 | 3/2015 | Radhakrishnan et al. |
| 2018/0280499 | A1 * | 10/2018 | Kimura ................. A61K 39/39 |

FOREIGN PATENT DOCUMENTS

| AU | 2013254940 A1 | 1/2014 |
| CN | 102512379 A * | 6/2012 |
| WO | WO-2009/140162 A1 | 11/2009 |
| WO | WO-2010/032011 A2 | 3/2010 |
| WO | WO-2010/110686 A1 | 9/2010 |

OTHER PUBLICATIONS

Machine translation of CN102512379A. pp. 1-16 (Year: 2012).*
Compounding Today. "https://compoundingtoday.com/TonicityAdjust/" Jan. 2006, pp. 1-2. (Year: 2006).*
Human translation of CN102512379A tables. pp. 1-14 (Year: 2012).*
Alexander et al., Antifungal resistance trends towards the year 2000. Implications for therapy and new approaches, Drugs, 54(5):657-78 (1997).
Briot et al., Stability of micafungin sodium solutions at different concentrations in glass bottles and syringes, Int. J. Pharm., 492:137-40 (2015).
Cancidas® (caspofungin acetate) for injection, Merck & Co., Inc. (2005).
European Medicines Agency, Assessment Report for Mycamine, Procedure No. EMEA/H/C/000734 (Apr. 24, 2008).
Mycamine Prescribing Information, Astellas Pharma, Inc. (Jun. 2013).
Vahdat et al., Kinetics of amoxicillin and clavulanate degradation alone and in combination in aqueous solution under frozen conditions, Int. J. Pharm., 342(1-2):95-104 (2007).
Zhu et al., Development and validation of a stability-indicating high performance liquid chromatographic (HPLC) method for the determination of related substances of micafungin sodium in drug substances, Int. J. Mol. Sci., 14(11):21202-14 (2013).
European Patent Application No. 17829412.0, Communication Pursuant to Article 94(3) EPC, dated Dec. 15, 2020.
European Patent Application No. 17829412.0, Communication Pursuant to Article 94(3) EPC, dated Jan. 24, 2023.
Costantino et al., "Lyophilization of Bioharmaceuticals" Springer Science & Business Media, Dec. 5, 2005.
European Patent Application No. 17829412.0, Communication Under Rule 71(3) EPC, Intent to Grant, dated Jul. 5, 2023.
Franks Felix et al, Chapter 3 "Essential Product and Process Parameters in Summary" Published by The Royal Society of Chemistry, 2007, pp. 20-27, London, UK.

(Continued)

Primary Examiner — Andrew S Rosenthal
(74) Attorney, Agent, or Firm — K&L Gates LLP

(57) ABSTRACT

An aqueous pharmaceutical composition suitable for parenteral administration and having enhanced storage stability includes between about 0.1 mg/mL and about 40 mg/mL micafungin; (ii) between about 0.1 mM and 400 mM buffering agent; and (iii) between about 0 mg/mL and about 500 mg/mL tonicity adjusting agent, wherein the pH of the composition is between about 3.0 and 7.0, for example, between about 3.5 and 7.0.

8 Claims, 3 Drawing Sheets

(56) References Cited

OTHER PUBLICATIONS

Izutsu Ken-Ichi, "Applications of Freezing and Freeze-Drying in Pharmaceutical Formulations" National Institute of Health Sciences, 2018, pp. 371-383, Kawasaki, Kanagawa.
Her Lin-Min et al., "Electrolyte-Induced Changes in Glass Transition Temperatures of Freeze-Concentrated Solutes" Phamaceutical Research, vol. 12, No. 5, 1995.
Challener Cynthia A. , "For Lyophilization, Excipients Really Do Matter" BioPharm International, BioPharm International Jan. 1, 2017, vol. 30, Issue 1.
"Best Practices in Formulation and Lyophilization Development", white paper edition, BioPharma Solutions, 2016, pp. 1-7.
Carpenter John F. et al., "Rational Design of Stable Lyophilized Protein Formulations: Some Practical Advice" Pharmaceutical Research, vol. 14, No. 8, 1997, pp. 969-975.

\* cited by examiner

MICAFUNGIN COMPOSITIONS

CROSS REFERENCE TO RELATED APPLICATION

This application claims the benefit under 35 U.S.C. § 119(e) of U.S. provisional patent application Ser. No. 62/435,695, filed Dec. 16, 2016, the entire disclosure of which is incorporated herein by reference, is hereby claimed.

FIELD OF THE DISCLOSURE

The disclosure relates generally to compositions comprising micafungin. More particularly, the disclosure is directed to aqueous compositions comprising micafungin having enhanced storage stability.

BRIEF DESCRIPTION OF RELATED TECHNOLOGY

Fungal infections, particularly systemic fungal infections in immunocompromised patients, present significant challenges for healthcare professionals. For example, well-established fungal infections are increasingly observed in patients undergoing organ transplants and in patients receiving chemotherapy (Alexander et al., Drugs, 54:657, 1997). Additionally, substantially all AIDS patients suffer from some form of fungal infection during the course of the disease (Alexander et al., Drugs, 54:657, 1997).

Echinocandins are a broad group of antifungal agents that are typically comprised of a cyclic hexapeptide core and a lipophilic tail that is attached to the cyclic hexapeptide core through an amide linkage. Echinocandins inhibit β-1,3-glucan synthase, which is a key enzyme in the synthesis of glucan in the cell wall of many fungi. Caspofungin, anidulafungin, and micafungin are echinocandins that have been approved for anti-fungal treatment. All three of these drugs are typically made semisynthetically, starting with natural products obtained through fermentation. Relatively poor intestinal absorption of these compounds requires that delivery is effected by infusion.

MYCAMINE® (micafungin sodium) for Injection is an intravenous infusion product manufactured by Astellas Pharma Inc. for the treatment of fungal infections. MYCAMINE® is provided as a lyophilized powder in 50 mg and 100 mg single-use vials. According to the prescribing information, each single-use vial contains 50 mg micafungin sodium or 100 mg micafungin sodium and 200 mg lactose. Two aseptic preparation steps must be strictly observed to administer the MYCAMINE® product. In the first aseptic preparation step, the lyophilized powder is reconstituted as a 10 mg/mL (50 mg vial) or 20 mg/mL (100 mg vial) concentrate in either isotonic saline (0.9 wt. %) or isotonic dextrose (5 wt. %). According to the prescribing information, the reconstituted product has a pH between 5-7 and may be stored for up to 24 hours at 25° C. The infusion product is then prepared by further diluting the reconstituted product in a second aseptic preparation step, typically to a concentration of 0.5-1.5 mg/mL in a 100 mL container. The diluted infusion product may also be stored for up to 24 hours at 25° C. Thus, the prescribing information teaches that MYCAMINE® should only be stored for a maximum of 24 hours after compounding for infusion.

U.S. Pat. No. 6,774,104 ("the '104 patent") discloses stabilized pharmaceutical compositions in lyophilized form containing echinocandin compounds such as micafungin. The '104 patent teaches that echinocandin compounds such as micafungin and their salts are unstable and must be lyophilized to prevent degradation. Specifically, the '104 patent explicitly teaches that echinocandin compounds are not "satisfactorily stable" to humidity and therefore compositions comprising echinocandin compounds cannot have more than 3.4 weight percent of water contained therein. Consistent with the teachings in the '104 patent, the instability of micafungin in water is again emphasized in Astellas Pharma's European Medicine Agency April 2008 Assessment Report for Mycamine: "[t]he results of micafungin stability in aqueous solution clearly indicate that the micafungin drug product could not be developed as a liquid dosage form."

The '104 patent further discloses that lyophilized compositions containing micafungin can be stabilized by using lyoprotectants, specifically, polysaccharides, disaccharides (such as lactose, maltose, and sucrose), and sodium chloride. Stability results in Tables 1 and 2 of the '104 patent demonstrate, however, that micafungin-containing compositions containing sucrose or sodium chloride performed relatively unsatisfactorily whereas formulations containing lactose or maltose demonstrated relatively good stability. The '104 patent does not disclose or suggest that monosaccharides may be used as lyoprotectants; indeed, the only monosaccharide-containing composition that was tested included glucose (most typically, glucose is present as D-glucose or dextrose) and reportedly experienced approximately 99% degradation after just 9 days.

SUMMARY

In one embodiment, the invention provides an aqueous pharmaceutical composition suitable for parenteral administration comprising between about 0.1 mg/mL and about 40 mg/mL micafungin; between about 0.1 mM and 400 mM buffering agent, for example, between about 0.5 mM and 400 mM; and between about 0 mg/mL and about 500 mg/mL tonicity adjusting agent, the composition having a pH between about 3.0 and about 7.0, for example, between about 3.5 and about 7.0.

In another embodiment, the invention provides a method of preparing an aqueous pharmaceutical composition suitable for parenteral administration comprising combining micafungin, buffering agent, and tonicity adjusting agent, to provide an aqueous pharmaceutical composition suitable for parenteral administration, the composition comprising between about 0.1 mg/mL and about 40 mg/mL micafungin; between about 0.1 mM and 400 mM buffering agent, for example, between about 0.5 mM and 400 mM; and between about 0 mg/mL and about 500 mg/mL tonicity adjusting agent, the composition having a pH between about 3.0 and about 7.0, for example, between about 3.5 and about 7.0.

BRIEF DESCRIPTION OF THE DRAWINGS

FIG. 3b shows a fitted curve showing expected total impurities over a pH range between about 3.0 and 7.0 based upon the actual data shown in FIG. 3a.

DETAILED DESCRIPTION

Figure 1:
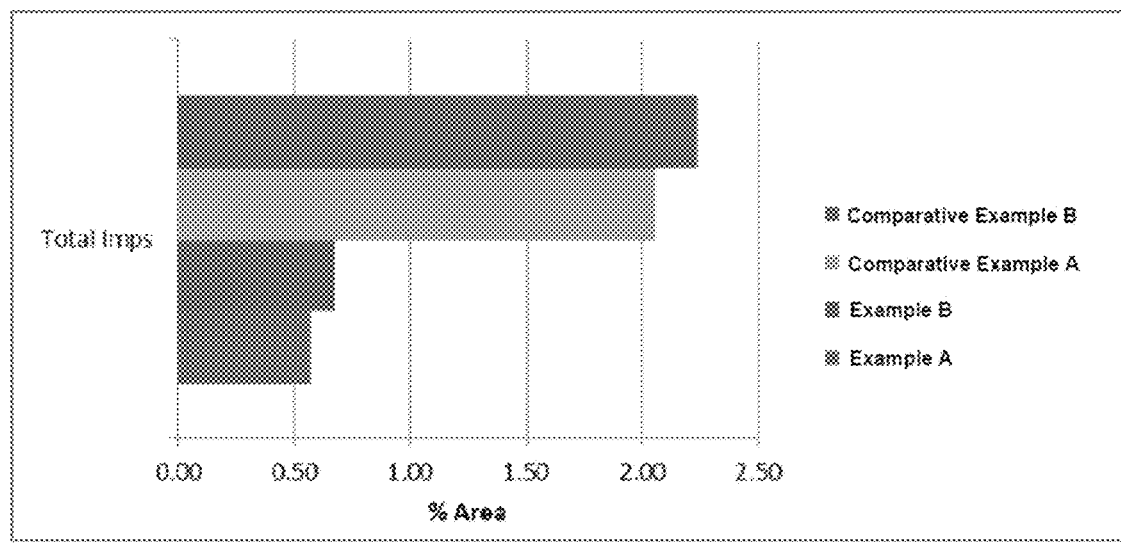
FIG. 1 illustrates the total impurities formed over two days at 25° C. in aqueous pharmaceutical compositions suitable for parenteral administration comprising micafungin according to the invention relative to comparable compositions comprising MYCAMINE®.

The present invention provides aqueous pharmaceutical compositions suitable for parenteral administration comprising micafungin. The compositions are formulated for parenteral administration and comprise between about 0.1 mg/mL and about 40 mg/mL micafungin; between about 0.1 mM and 400 mM buffering agent, for example, between about 0.5 mM and 400 mM; and between about 0 mg/mL and about 500 mg/mL tonicity adjusting agent. The pH of the compositions is between about 3.0 and about 7.0, for example, between about 3.5 and about 7.0. In one aspect, the aqueous pharmaceutical compositions suitable for parenteral administration comprising micafungin are "ready-to-use" such that they can be administered parenterally without any further compounding or processing, thereby advantageously avoiding any additional aseptic compounding or processing of the compositions prior to administration. Thus, the aqueous pharmaceutical compositions suitable for parenteral administration can be formulated and packaged in a sealed container such that they are ready-to-use, for example, as an intravenous infusion. Pharmaceutical compositions suitable for parenteral administration comprising micafungin according to the invention can be frozen and yet still considered ready-to-use provided that no further compounding or processing is needed prior to administration.

In another aspect, the aqueous pharmaceutical compositions suitable for parenteral administration comprising micafungin are provided as "concentrate" compositions which typically are diluted prior to being parenterally administered.

As demonstrated in the Examples, the aqueous pharmaceutical compositions suitable for parenteral administration comprising micafungin according to the invention possess surprisingly enhanced storage stability, particularly relative to compositions comprising MYCAMINE® which are reconstituted according to the label directions. Furthermore, the stability of these compositions is surprising and unexpected in view of the prior art teachings that micafungin is unstable in aqueous solution as mentioned above. Because of their enhanced storage stability, the compositions according to the invention advantageously can be stored for relatively long periods, particularly relative to teaching that MYCAMINE® should only be stored for a maximum of 24 hours after compounding for infusion. Such enhanced storage stability is useful for storing both ready-to-use and concentrate compositions according to the invention and can minimize or even eliminate the need for additional compounding/processing of the compositions, thereby minimizing or even eliminating the requirement for aseptic processing of the compositions prior to administration.

As mentioned in the background section above, micafungin is an echinocandin compound. Echinocandin compounds are structurally related in that they include a cyclic hexapeptide and a lipophilic tail that is attached to the cyclic hexapeptide core through an amide linkage. As a class, echinocandin compounds typically demonstrate anti-fungal activity. Despite these common structural and functional characteristics, however, as shown in the Examples, all echinocandin compound-containing compositions surprisingly do not demonstrate the enhanced storage stability of the compositions comprising micafungin according to the invention. Specifically, as shown in the examples, aqueous compositions comprising micafungin according to the invention demonstrate enhanced storage stability whereas comparable aqueous compositions comprising caspofungin (which like micafungin is also an echinocandin compound) demonstrate unacceptable degradation of the caspofungin active agent.

Further, as demonstrated in the Examples, the inventors found that the pH of the aqueous pharmaceutical compositions comprising micafungin according to the invention can greatly affect the stability of the micafungin contained in the compositions. Specifically, pH values that are too low or too high can significantly affect the stability of the micafungin-containing compositions. The pH of the aqueous pharmaceutical compositions should be between about 3.0 and about 7.0, between about 3.5 and about 7.0, between about 3.6 and about 6.8, between about 3.6 and about 6.4, between about 3.8 and about 6.2, preferably between about 4.0 and about 6.0, and more preferably between about 4.5 and about 5.5. The pH can be adjusted as known in the art, for example, by addition of sodium hydroxide or hydrochloric acid.

The aqueous pharmaceutical compositions suitable for parenteral administration disclosed herein are preferably stable compositions. As used herein, the term "stable" refers to an aqueous pharmaceutical composition that remains suitable for parenteral administration to a patient over a given period of time, typically over the shelf life of the product. In this respect, because of their enhanced stability, the aqueous pharmaceutical compositions suitable for parenteral administration disclosed herein can advantageously be stored frozen for extended periods of time, for example, for more than 6 months, and then optionally stored at low temperature or even room temperature for significant time periods, without significant degradation of the micafungin contained therein.

For example, in one aspect, as determined by HPLC analysis, the aqueous pharmaceutical compositions according to the present invention may be considered to be stable when the compositions include less than 1.0 area % impurities, for example, less than 0.50 area % impurities, after being frozen (−20° C.) for at least 24, or more preferably for at least 48 weeks (with the time periods being measured from formulation of the aqueous pharmaceutical compositions according to the present invention), based on the initial amount of micafungin present in the composition. Alternatively, as determined by HPLC analysis, the aqueous pharmaceutical compositions according to the present invention may be considered to be stable when the compositions include at least 99.0 area % micafungin, for example, at least 99.5 area % micafungin, after being frozen (−20° C.) for at least 24, or more preferably for at least 48 weeks (with the time periods being measured from formulation of the aqueous pharmaceutical compositions according to the present invention), based on the initial amount of micafungin present in the composition. As used herein, "formulation of the aqueous pharmaceutical compositions according to the present invention" refers to the process of combining of micafungin, buffering agent, tonicity adjusting agent, and any added aqueous diluent in order to prepare an aqueous pharmaceutical composition suitable for parenteral administration. The point at which the aqueous pharmaceutical composition suitable for parenteral administration is prepared is considered "time 0" and any time periods that the composition is referenced as being stable is measured relative thereto.

In another aspect, as determined by HPLC analysis, the aqueous pharmaceutical compositions according to the present invention may be considered to be stable when the compositions include less than about 5% area total impurities after storage thereof at room temperature for three weeks, or less than 2.5 area % impurities, for example, less than 1.5 area % impurities, after being maintained at room temperature (25° C.) for at least four weeks (with the time periods being measured from formulation of the aqueous pharmaceutical compositions according to the present invention), based on the initial amount of micafungin present in the composition. Alternatively, as determined by HPLC analysis, the aqueous pharmaceutical compositions according to the present invention may be considered to be stable when the compositions include at least 97.5 area % micafungin, for example, at least 98.5 area % micafungin, after being maintained at room temperature (25° C.) for at least four weeks (with the time periods being measured from formulation of the aqueous pharmaceutical compositions according to the present invention), based on the initial amount of micafungin present in the composition.

In yet another aspect, the aqueous pharmaceutical compositions according to the present invention may be considered to be stable when the compositions include less than 2.0 area % impurities, for example, less than 1.0 area % impurities, as determined by HPLC analysis after being maintained at low temperature (5° C.) for at least 24, or more preferably for at least 64 weeks (with the time periods being measured from formulation of the aqueous pharmaceutical compositions according to the present invention), based on the initial amount of micafungin present in the composition. Alternatively, the aqueous pharmaceutical compositions according to the present invention may be considered to be stable when the compositions include at least 98.0 area % micafungin, for example, at least 99.0 area % micafungin, as determined by HPLC analysis after being maintained at low temperature (5° C.) for at least 24, or more preferably for at least 64 weeks (with the time periods being measured from formulation of the aqueous pharmaceutical compositions according to the present invention), based on the initial amount of micafungin present in the composition.

As described above, the pH of the aqueous pharmaceutical compositions according to the present invention can greatly affect the stability, and thereby the purity of the micafungin-containing compositions. Thus, in another aspect, the aqueous pharmaceutical compositions according to the present invention may be considered to be stable when the aqueous pharmaceutical composition changes by less than 1 pH unit, by less than 0.5 pH units, by less than 0.1 pH unit, or more preferably by less than 0.05 pH units over a period of at least 9 days at room temperature (with the time periods being measured from formulation of the aqueous pharmaceutical compositions according to the present invention). Any conventional properly calibrated potentiometric sensor and measuring system can be used to measure pH as is known in the art and described in USP 791.

Figure 3A:
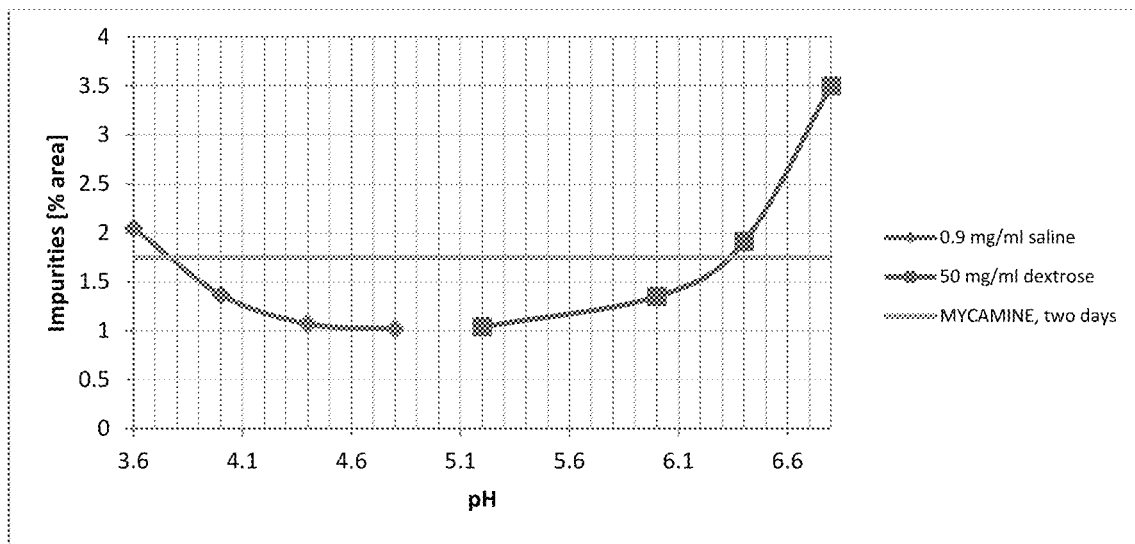
FIG. 3a shows total impurities for aqueous pharmaceutical compositions suitable for parenteral administration comprising micafungin according to the invention at various pH values.
Figure 3B:
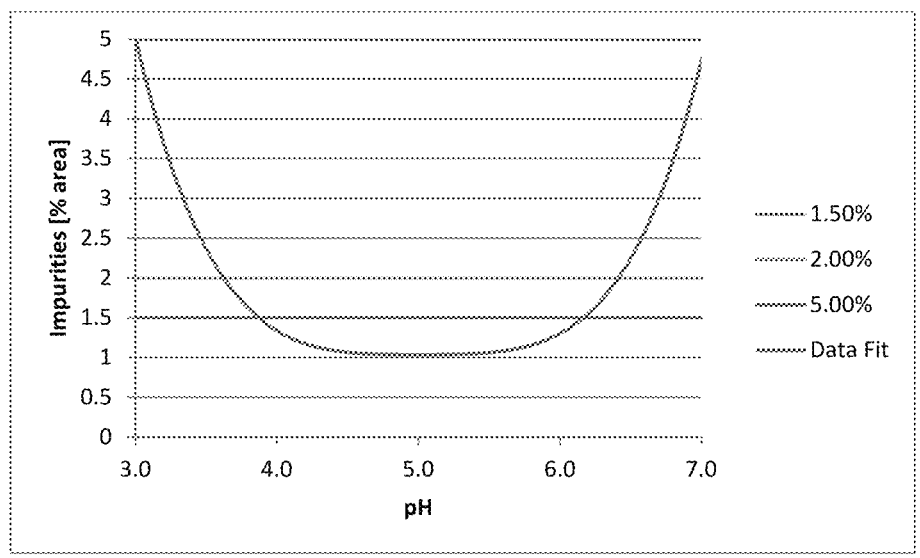

As shown with reference to FIGS. 3a and 3b, in embodiments, as determined by HPLC analysis, the aqueous pharmaceutical composition according to the invention may have less than about 5% area total impurities after formulation and storage thereof at room temperature for three weeks, when the composition has a pH at time 0 between about 3.0 and about 7.0. In another embodiment, the aqueous pharmaceutical composition may have less than 2.0% area total impurities after formulation and storage thereof at room temperature for three weeks, wherein the composition has a pH at time 0 between about 3.6 and about 6.4. In a more preferred embodiment, the aqueous pharmaceutical composition may have less than 1.5% area total impurities after formulation and storage thereof at room temperature for three weeks, wherein the composition has a pH at time 0 between about 3.8 and about 6.2.

The aqueous pharmaceutical compositions suitable for parenteral administration disclosed herein are preferably sterile compositions. As used herein, the term "sterile" refers to a composition that has been brought to a state of sterility and has not been subsequently exposed to microbiological contamination, e.g., a container holding the sterile composition does not contain replicating microorganisms and has not been compromised such that it has been exposed to ambient atmosphere and/or biological contaminants. In pharmaceutical practice, a state of sterility exists when the probability is less than one out of one million that the composition is contaminated with replicating microorganisms. Sterile compositions in accordance with the invention are generally prepared in accordance with current Good Manufacturing Practice ("CGMP") regulations of the U.S. Food and Drug Administration.

In each of the embodiments described herein, the micafungin in the aqueous pharmaceutical compositions suitable for parenteral administration comprising micafungin according to the invention may be provided as a free acid or as a pharmaceutically acceptable salt. The salt may be an alkali metal salt (e.g., a sodium salt, a potassium salt, etc.), an alkaline earth metal salt (e.g., a calcium salt, a magnesium salt, etc.), an ammonium salt, an organic base salt such as an organic amine salt (e.g., a triethylamine salt, a diisopropylethylamine salt, a pyridine salt, a picoline salt, an ethanolamine salt, a triethanolamine salt, a dicyclohexylamine salt, a N,N'-dibenzylethylenediamine salt). Most typically, the micafungin is provided as the sodium salt, i.e., as micafungin sodium. 100 mg of micafungin is equivalent to 101.73 mg micafungin sodium.

In each of the embodiments described herein, the compositions comprising micafungin according to the invention may be substantially free of lyoprotectants including but not limited to disaccharides and polysaccharides. For example, the compositions according to the invention may be substantially free of lactose, maltose, and/or sucrose. In another example, the compositions according to the invention may be substantially free of lactose. As used herein, "substantially free of lyoprotectants", "substantially free of lactose, maltose, and/or sucrose" and "substantially free of lactose" means that the micafungin-containing compositions according to the invention contain insignificant amounts of disaccharides and polysaccharides or contain insignificant amounts of the specifically listed lyoprotectant(s). For example, the micafungin-containing compositions according to the disclosure may contain less than 0.10 weight percent, less than 0.05 wt. %, or less than 0.001 wt. %, of disaccharides and polysaccharides, based on the entire weight of the composition. Similarly, the micafungin-containing compositions according to the disclosure may contain less than 0.10 weight percent, less than 0.05 wt. %, or less than 0.001 wt. %, of lactose, maltose, and/or sucrose, based on the entire weight of the composition. Still further, the micafungin-containing compositions according to the disclosure may contain less than 0.10 weight percent, less than 0.05 wt. %, or less than 0.001 wt. %, of lactose, based on the entire weight of the composition.

As discussed above, the compositions comprising micafungin according to the invention can be provided as sterile, ready-to-use compositions suitable for infusion, thereby avoiding the inconvenience of diluting a concentrate composition into infusion diluents prior to infusion, as well as eliminating the risk of microbiological contamination during aseptic handling and any potential calculation or dilution error. Because no additional compounding is required, ready-to-use aqueous pharmaceutical compositions suitable for parenteral administration comprising micafungin according to the invention advantageously can also prevent medication errors resulting from improper compounding (and thus subsequent administration of an improper dose). In addition, ready-to-use compositions comprising micafungin according to the invention can advantageously be stored frozen for extended periods of time, for example, for more than 6 months, for more than 12 months, and/or even for more than 18 months after formulation thereof, without substantial degradation of the micafungin contained therein, and then thawed and administered without any further compounding. Because the pharmaceutical compositions according to the invention possess surprisingly enhanced storage stability, particularly relative to teaching that MYCAMINE® should only be stored for a maximum of 24 hours after compounding for infusion, the compositions can be administered after more than week, after more than two weeks, after more than three weeks, and even after four weeks post-thawing, which is a significant benefit to hospitals, doctor offices, and other healthcare facilities that treat fungal infections.

Alternatively, the compositions comprising micafungin according to the invention can be provided as concentrated compositions which must be diluted prior to administration.

Micafungin is present in the aqueous pharmaceutical compositions suitable for parenteral administration according to the invention in an amount between about 0.1 mg/ml and about 40 mg/ml. Ready-to-use aqueous pharmaceutical compositions according to the invention may contain between about 0.1 mg/ml and about 5 mg/ml micafungin, between about 0.5 mg/ml and about 2.5 mg/ml, for example, about 1 mg/ml. Concentrate aqueous pharmaceutical compositions according to the invention may contain between about 5 mg/ml and about 40 mg/ml micafungin, between about 5 mg/ml and about 20 mg/ml, for example, 10 mg/ml.

Suitable buffers are well-known in the art and are present in the aqueous pharmaceutical compositions suitable for parenteral administration comprising micafungin according to the invention to maintain a composition pH between about 3.5 and about 7.0 over a period of time, for example, over the shelf life of the product. Buffers usually include a weak acid and its conjugate base in relatively similar quantities and thus can be prepared by providing these components in combination. Buffers can also be generated in situ by providing only one of the weak acid and the conjugate base and adjusting the composition according to the invention to have a pH value between about 3.0 and about 7.0, between about 3.5 and about 7.0, between about 3.6 and about 6.8, between about 3.6 and about 6.4, between about 3.8 and about 6.2, preferably between about 4.0 and about 6.0, and more preferably between about 4.5 and about 5.5. As used herein, the term "buffering agent" refers to a weak acid, a conjugate base of the weak acid, and combinations of the foregoing. Typically, a buffering agent is present in the aqueous pharmaceutical compositions suitable for parenteral administration comprising micafungin according to the invention in a concentration ranging between about 0.1 mM and about 400 mM, or about 0.5 mM and about 400 mM, for example, between about 0.1 mM and about 100 mM, between about 0.5 mM and about 100 mM, between about 1 mM and about 100 mM, and/or between 10 mM and 100 mM. Ready-to-use aqueous pharmaceutical compositions suitable for parenteral administration comprising micafungin according to the invention typically have buffering agent concentrations of about 0.1 mM and about 20 mM, about 0.5 mM and about 20 mM, about 1 mM and about 20 mM, between about 5 mM and about 15 mM, for example, about 10 mM. Concentrate aqueous pharmaceutical compositions suitable for parenteral administration comprising micafungin according to the invention typically have buffering agent concentrations between about 20 mM and about 400 mM, between about 20 mM and about 200 mM, for example, about 25 mM or about 100 mM. Unexpectedly, ascorbic acid-based (ascorbate) buffers are preferably avoided. More specifically, it is believed that ascorbic-acid based buffering agents and other buffering agents capable of providing antioxidant activity should be avoided. Exemplary suitable buffering agents include acetate, glutamate, citrate, tartrate, benzoate, lactate, gluconate, phosphate, glycine, histidine, succinate, methane sulfonate, maleate, aspartate, carbonate, bicarbonate, and combinations thereof. A preferred buffering agent comprises sodium citrate.

Suitable tonicity adjusting agents are well-known in the art, and are present in the aqueous pharmaceutical compositions suitable for parenteral administration comprising micafungin according to the invention in order to render the compositions isotonic with physiological fluids. Typically, the tonicity adjusting agent is present in the aqueous pharmaceutical compositions suitable for parenteral administration comprising micafungin according to the invention in an amount ranging from about 0 mg/ml to about 500 mg/ml. Exemplary tonicity adjusting agents include sodium chloride, dextrose, mannitol, glycerine, Ringer's solution, and combinations of the foregoing. Sodium chloride and dextrose are preferred tonicity adjusting agents. In view of the teachings in the '104 patent discussed above, the enhanced stability of aqueous pharmaceutical compositions suitable for parenteral administration comprising micafungin according to the invention further comprising dextrose is particularly surprising and unexpected.

Ready-to-use aqueous pharmaceutical compositions suitable for parenteral administration comprising micafungin according to the invention may contain about 1 mg/ml to about 100 mg/ml tonicity adjusting agent, for example, about 4 mg/ml to about 60 mg/ml tonicity adjusting agent. In one embodiment, ready-to-use aqueous pharmaceutical compositions suitable for parenteral administration comprising micafungin according to the invention may contain about 4 to about 10 mg/ml sodium chloride. In another embodiment, ready-to-use aqueous pharmaceutical compositions suitable for parenteral administration comprising micafungin according to the invention may contain dextrose, with or without sodium chloride, in an amount ranging from about 25 mg/ml to about 60 mg/ml dextrose. When present in combination with sodium chloride, dextrose is preferably present in the ready-to-use aqueous pharmaceutical compositions suitable for parenteral administration comprising micafungin according to the invention at a level less than or equal to about 50 mg/ml and the sodium chloride is preferably present at a level less than or equal to about 9 mg/ml.

Concentrate aqueous pharmaceutical compositions suitable for parenteral administration comprising micafungin according to the invention may contain up to about 500 mg/ml, for example, between about 5 mg/mL and 250 mg/mL, or between about 2.5 mg/mL and 250 mg/mL tonicity adjusting agent.

In one embodiment, a tonicity adjusting agent is not present in concentrate aqueous pharmaceutical compositions suitable for parenteral administration comprising micafungin according to the invention. Such concentrate compositions can be mixed, for example, directly into a saline bag or dextrose bag to facilitate parenteral administration of the compositions at a suitable tonicity for parenteral administration without further compounding.

The aqueous pharmaceutical compositions comprising micafungin according to the invention are suitable for parenteral administration to a patient. For example, the aqueous pharmaceutical compositions comprising micafungin according to the invention may be administered in the form of a bolus injection or intravenous infusion. Suitable routes for parenteral administration include intravenous, subcutaneous, intradermal, intramuscular, intraarticular, and intrathecal. The ready-to-use aqueous pharmaceutical compositions comprising micafungin according to the invention are preferably administered by intravenous infusion.

The aqueous pharmaceutical compositions suitable for parenteral administration comprising micafungin according to the invention may be packaged in any suitable container known in the art including but not limited to vials, syringes, bags, bottles and ampules presentations. Containers may be fabricated from glass or from polymeric materials.

The dosage forms can be held in any suitable container with sizes typically ranging from 1 ml to 500 ml. Ready-to-use aqueous pharmaceutical compositions suitable for parenteral administration according to the invention are typically filled into bags, bottles, ampules, or vials with sizes generally between 1 ml and 500 ml, for example, 50 mL or 100 mL bags. In addition, pre-filled syringes can be used as the container for ready-to-use aqueous pharmaceutical compositions suitable for parenteral administration according to the invention. Concentrate aqueous pharmaceutical compositions suitable for parenteral administration according to the invention can be contained in bags, bottles, ampules, or bottles with sizes generally between 1 ml and 50 ml, for example, 10 mL vials.

Polymeric containers are preferably flexible and can contain or be free of polyvinylchloride (PVC). Preferred containers are free of PVC, such as those disclosed in U.S. Pat. Nos. 5,849,843 and 5,998,019. Suitable flexible polymeric containers include but are not limited to GALAXY IV containers (Baxter International Inc.) and INTRAVIA containers (Baxter International Inc.). Polymeric containers can further be provided with a barrier as a secondary packaging system to prevent the loss of water during storage, to protect against light-induced degradation, and/or to further ensure the stability of the aqueous pharmaceutical compositions suitable for parenteral administration comprising micafungin according to the invention. A preferred barrier is a cardboard carton. Other barriers such as an aluminum overpouch, light absorbing polymeric overpouches, and similar barrier structures could also be used.

Procedures for filling aqueous pharmaceutical compositions suitable for parenteral administration comprising micafungin according to the invention in containers, and their subsequent processing are known in the art. Such procedures are well known and are often used to produce sterile pharmaceutical injectable drug products. Sterile pharmaceutical compositions according to the present invention may be prepared using aseptic processing techniques. Aseptic filling is ordinarily used to prepare drug products that will not withstand heat sterilization, but in which all of the ingredients are sterile. Sterility is maintained by using sterile materials and a controlled working environment. All containers and apparatus are sterilized, preferably by heat sterilization or by being exposed to a peroxide bath, prior to filling. The container (e.g., vial, ampule, bag, bottle, or syringe) is then filled under aseptic conditions. Sterilization can be conducted by, for example, by filtration through a bacteria retaining filter, by incorporating sterilizing agents into the compositions, and using other known techniques.

The containers including aqueous pharmaceutical compositions suitable for parenteral administration disclosed herein may be stored at any suitable temperature, for example, at room temperature or at a low temperature, for example, at a temperature between about −25° C. and about 25° C. Lower temperatures, particularly below freezing, are preferred for long term storage.

The following examples are provided to illustrate the aqueous pharmaceutical compositions suitable for parenteral administration comprising micafungin according to the invention, but are not intended to limit the scope thereof.

Example 1: Impurity Formation Comparison with Mycamine®

A stability study was carried out on aqueous pharmaceutical compositions suitable for parenteral administration comprising micafungin according to the invention and comparative compositions comprising MYCAMINE® (micafungin sodium) by measuring impurity formation in the various samples. Specifically, the impurities that formed in Example Compositions A and B comprising 1.0 mg/mL micafungin sodium in 0.9% (w/v) saline or 5% (w/v) dextrose, respectively, and buffered with 10 mM citrate buffer, and the impurities that formed in Comparative Example Compositions A and B, which were prepared using a single-use MYCAMINE® (micafungin sodium) vial containing 100 mg micafungin sodium, at a concentration of 1.0 mg/mL micafungin sodium, were determined. The buffer was prepared by combining 6 mM citrate and 4 mM citric acid and adjusting with hydrochloric acid or sodium hydroxide to arrive at the indicated pH. The formulations for Example Compositions A and B and Comparative Example Compositions A and B are provided in Table I, below.

TABLE I

| Component | Example A | Example B | Comparative Example A | Comparative Example B |
| --- | --- | --- | --- | --- |
| Active Agent | 1.0 mg/mL micafungin sodium | 1.0 mg/mL micafungin sodium | 1.0 mg/mL micafungin sodium (diluted MYCAMINE®) | 1.0 mg/mL micafungin sodium (diluted MYCAMINE®) |
| Buffer | 10 mM citrate | 10 mM citrate | N/A | N/A |
| pH | 4.78 | 4.76 | 5.69 | 5.54 |
| Excipient | None | None | 2.0 mg/mL lactose (diluted MYCAMINE®) | 2.0 mg/mL lactose (diluted MYCAMINE®) |

TABLE I-continued

| Component | Example A | Example B | Comparative Example A | Comparative Example B |
|---|---|---|---|---|
| Tonicity adjusting agent | 9 mg/mL saline | 50 mg/mL dextrose | 9 mg/L saline | 50 mg/mL dextrose |

Example Compositions A and B and Comparative Example Compositions A and B were conditioned at 25° C. for two days. Impurities were measured using high-performance liquid chromatography based on a method described in Zhu et al., Int. J. Mol. Sci. 2013, 14, 21202-21214. The chromatographic separation was achieved on an Agilent 1100 Series HPLC with a SB column (250×4.6 mm, 5 µm), using a mobile phase of sodium phosphate with sodium perchlorate, adjusted to pH 2.9 with phosphoric acid in combination with acetonitrile (62:38 v/v).

Figure 2:
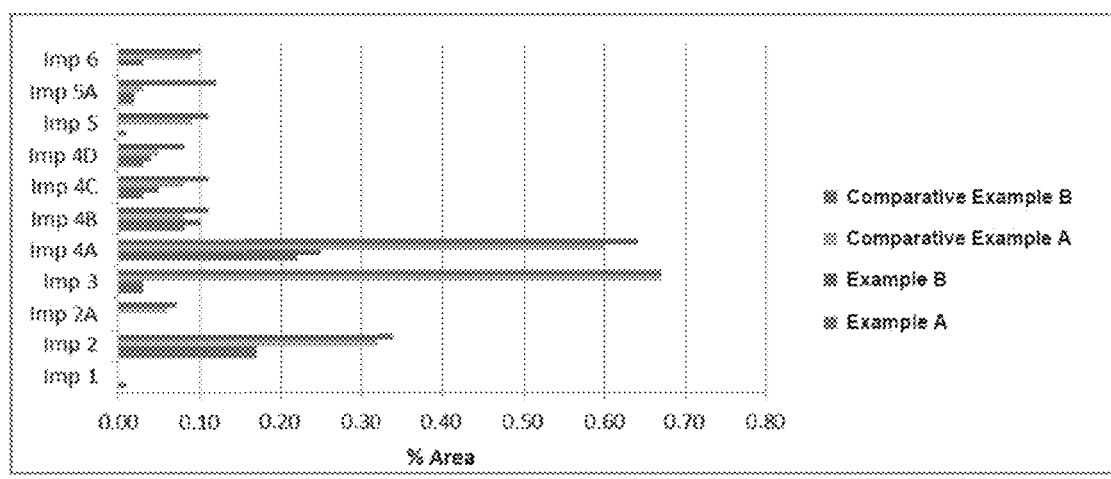
FIG. 2 illustrates the individual impurities formed over two days at 25° C. in aqueous pharmaceutical compositions suitable for parenteral administration comprising micafungin according to the invention relative to comparable compositions comprising MYCAMINE®.

As shown in FIG. 1, significantly less impurity formation was observed in Examples A and B, the aqueous pharmaceutical compositions suitable for parenteral administration comprising micafungin according to the invention, relative to Comparative Example Compositions A and B containing MYCAMINE®, thereby demonstrating the surprisingly enhanced stability of the micafungin-containing compositions according to the invention. FIG. 2 illustrates that individual impurity formation for pharmaceutical compositions suitable for parenteral administration comprising micafungin according to the invention was also typically significantly less or at worst approximately the same relative to comparable compositions comprising MYCAMINE®. Table II, below, shows the experimental data used to generate FIGS. 1 and 2.

TABLE II

|  | Example A | Example B | Comparative Example A | Comparative Example B |
|---|---|---|---|---|
| Imp 1 | 0.01 | 0.00 | 0.00 | 0.00 |
| Imp 2 | 0.17 | 0.17 | 0.32 | 0.34 |
| Imp 2A | 0.00 | 0.00 | 0.06 | 0.07 |
| Imp 3 | 0.03 | 0.03 | 0.67 | 0.67 |
| Imp 4A | 0.22 | 0.25 | 0.60 | 0.64 |
| Imp 4B | 0.08 | 0.10 | 0.08 | 0.11 |
| Imp 4C | 0.03 | 0.05 | 0.08 | 0.11 |
| Imp 4D | 0.03 | 0.04 | 0.05 | 0.08 |
| Imp 5 | 0.01 | 0.00 | 0.09 | 0.11 |
| Imp 5A | 0.02 | 0.02 | 0.03 | 0.12 |
| Imp 6 | 0.00 | 0.03 | 0.09 | 0.10 |
| Total Impurities, mol. % area | 0.57 | 0.67 | 2.06 | 2.23 |

This example demonstrates that the pharmaceutical compositions suitable for parenteral administration comprising micafungin according to the invention are surprisingly stable in that significantly less impurity formation is observed, particularly relative to comparable compositions comprising MYCAMINE®. In fact, three times as many impurities were observed in the comparable compositions relative to the compositions suitable for parenteral administration comprising micafungin according to the invention.

Example 2: Stability Comparison with Cancidas®

A stability study was carried out on aqueous pharmaceutical compositions suitable for parenteral administration comprising micafungin according to the invention and comparative compositions comprising CANCIDAS® (caspofungin acetate) by measuring the active agent concentration in the various samples. Specifically, the active agent concentrations of Example Compositions A and B comprising 1.0 mg/mL micafungin sodium in 0.9% (w/v) saline or 5% (w/v) dextrose, respectively, and buffered with 10 mM citrate buffer, and of Comparative Example Compositions C and D comprising 1.0 mg/mL caspofungin acetate (CANCIDAS®) in 0.9% (w/v) saline or 5% (w/v) dextrose, respectively, also buffered with 10 mM citrate buffer, were measured at several time points. As mentioned above, both micafungin and caspofungin are echinocandins which share structural and functional characteristics. The formulations for Example Compositions A and B and Comparative Example Compositions C and D are provided in Table III, below.

TABLE III

| Component | Example A | Example B | Comparative Example C | Comparative Example D |
|---|---|---|---|---|
| Active Agent | 1.0 mg/mL micafungin sodium | 1.0 mg/mL micafungin sodium | 1.0 mg/mL caspofungin acetate (diluted CANCIDAS ®) | 1.0 mg/mL caspofungin acetate (diluted CANCIDAS ®) |
| Buffer | 10 mM citrate | 10 mM citrate | 10 mM citrate | 10 mM citrate |
| pH | 4.78 | 4.76 | 4.78 | 4.78 |
| Excipient | None | None | 0.78 mg/mL sucrose & 0.52 mg/mL mannitol (diluted CANCIDAS ®) | 0.78 mg/mL sucrose & 0.52 mg/mL mannitol (diluted CANCIDAS ®) |
| Tonicity adjusting agent | 9 mg/mL saline | 50 mg/mL dextrose | 9 mg/mL saline | 50 mg/mL dextrose |

Example Compositions A and B and Comparative Example Compositions C and D were conditioned at 25° C. for eight days, with samples taken at 0, 2 days, and 8 days.

tration of 10.0 mg/mL micafungin sodium, were determined. The formulations for Example Compositions C and D and Comparative Example E are provided in Table V, below.

TABLE V

| Component | Example C | Example D | Comparative Example E |
|---|---|---|---|
| Active Agent | 10.0 mg/mL micafungin sodium | 10.0 mg/mL micafungin sodium | 10.0 mg/mL micafungin sodium (diluted MYCAMINE ®) |
| Buffer | 25 mM citrate | 100 mM citrate | N/A |
| pH | 4.80 | 4.80 | 5.29 |
| Lyoprotectant | None | None | 20 mg/mL lactose (diluted MYCAMINE ®) |
| Tonicity adjusting agent | 9 mg/mL saline | 9 mg/mL saline | 9 mg/mL saline |

The concentration of the active agents in Example Compositions A and B were measured using the high-performance liquid chromatography method described in Example 1. The concentrations of the active agents in Comparative Examples C and D were measured using another similar HPLC method adapted for measuring the impurities in samples containing caspofungin acetate. As shown in Table IV below, the concentration values were measured in Example Compositions A and B, the aqueous pharmaceutical compositions suitable for parenteral administration comprising micafungin according to the invention, and in Comparative Examples C and D comprising CANCIDAS®.

This example demonstrates that the pharmaceutical compositions suitable for parenteral administration comprising micafungin according to the invention are surprisingly stable, particularly relative to comparable compositions comprising CANCIDAS®, in which unacceptable degradation of the caspofungin active agent was observed.

TABLE IV

| | Days | | |
|---|---|---|---|
| | 0 | 2 | 8 |
| Example A, % of initial active agent concentration | 100 | 100.18 | 99.72 |
| Example B, % of initial active agent concentration | 100 | 100.09 | 99.45 |
| Comparative Example C, % of initial active agent concentration | 100 | 75.39 | 57.40 |
| Comparative Example D, % of initial active agent concentration | 100 | 88.33 | 73.33 |

Example 3: Impurity Formation Comparison with Mycamine®

A stability study was carried out on vials containing either concentrated aqueous pharmaceutical compositions suitable for parenteral administration comprising micafungin according to the invention or concentrated comparative compositions comprising MYCAMINE® (micafungin sodium) by measuring impurity formation in the various samples after conditioning the samples for one month at 25° C. Specifically, the active agent concentrations and the impurities that formed in Examples C and D comprising 10 mg/mL micafungin sodium in 0.9% (w/v) saline and buffered with 25 mM or 100 mM citrate buffer, respectively, and the impurities that formed in Comparative Example E, which was prepared using a single-use MYCAMINE® (micafungin sodium) vial containing 100 mg micafungin, at a concen- Example Compositions C and D and Comparative Example E were conditioned at 25° C. for one month. Impurities were measured using the high-performance liquid chromatography method described in Example 1. As shown in Table VI, below, significantly less impurity formation was observed in Examples C and D, the aqueous pharmaceutical compositions suitable for parenteral administration comprising micafungin according to the invention, relative to Comparative Example E containing MYCAMINE®. Indeed, impurities formed nearly three times as often in the comparative example formulation relative to the concentrated compositions comprising micafungin according to the invention.

TABLE VI

| | Example C | Example D | Comparative Example E |
|---|---|---|---|
| Total Impurities, % area | 0.96 | 0.98 | 2.63 |
| Micafungin, % area | 98.98 | 98.95 | 97.17 |

This example demonstrates that the pharmaceutical compositions suitable for parenteral administration comprising micafungin according to the invention are surprisingly stable in that significantly less impurity formation is observed, particularly relative to comparable compositions comprising MYCAMINE®.

Example 4: pH Studies

Non-isothermal kinetics studies were carried out on aqueous pharmaceutical compositions suitable for parenteral administration comprising micafungin according to the invention.

Specifically, the non-isothermal kinetics of pharmaceutical compositions suitable for parenteral administration comprising 1.0 mg/mL micafungin sodium in 5% (w/v) dextrose and buffered with 20 mM buffer were explored at pH values of 4.0, 5.0, and 6.0 using a Berkeley Madonna algorithm. The temperature cycle was 40° C. to 80° C. over 6 hours and the experiments were conducted to approximately 30% degradation. As shown below in Table VII, compositions suitable for parenteral administration comprising micafungin according to the invention were most stable in dextrose at pH 5.0, at least relative to comparable compositions at pH values of 4.0 and 6.0.

TABLE VII

| pH | Micafungin Degradation in dextrose [%] | Duration [hr] | AVE Degradation [%/hr] |
|---|---|---|---|
| 4.0 | 29 | 32.5 | 0.9 |
| 5.0 | 30 | 53.5 | 0.6 |
| 6.0 | 35 | 22 | 1.6 |

An additional study determined the impurity profiles of aqueous pharmaceutical compositions suitable for parenteral administration comprising 1.0 mg/ml micafungin in 5% (w/v) dextrose and buffered with 10 mM buffer, with the pH of the compositions being adjusted to different values (5.2, 5.5, and 5.8). Prior to testing, the sample compositions were frozen (−20° C.) and stored for over 8 months, and then thawed by conditioning at 25° C. for 1 week while being protected from light. All three sample compositions demonstrated similar impurity profiles such that a significant difference was not observed in the impurity profiles.

This example demonstrates that the pharmaceutical compositions suitable for parenteral administration comprising micafungin in dextrose according to the invention are significantly more stable at pH values of about 5.0, particularly relative to comparable compositions at a pH value 6.0. This example further demonstrates that pharmaceutical compositions suitable for parenteral administration comprising micafungin according to the invention demonstrate similarly acceptable stabilities at pH values of 5.2, 5.5, and 5.8.

Example 5: Buffer Study 1.0 mg/mL micafungin sodium formulations were prepared and filled into Galaxy containers (filled to 40 mL) or vials (filled to 2.5 mL) at pH 5.0. The buffer and the tonicity adjusting agent were varied as shown in Table VIII, below.

TABLE VIII

| Example | Tonicity adjusting agent | Buffer | Conc [mM] |
|---|---|---|---|
| E | 50 mg/mL dextrose | Citrate | 10 |
| F | 9 mg/mL saline | Citrate | 10 |
| G | 50 mg/mL dextrose | Acetate | 10 |
| H | 50 mg/mL dextrose | Cystine/Citrate | 10 |
| I | 50 mg/mL dextrose | Ascorbic Acid | 10 |

Example Compositions E, F, G, H, and I were frozen overnight (−20° C.) and then conditioned at 25° C. for 14 days, with samples taken at time 0, 3 days, 7 days, and 14 days. The impurities in the various samples were monitored using the HPLC method described in Example 1. It was unexpectedly found that buffers comprising ascorbic acid performed poorly relative to other buffers as shown in Table IX, below. Indeed, at 14 days, impurities formed up to amounts greater than two times as often in the example formulation comprising ascorbic acid relative to the other buffers tested.

TABLE IX

| | Total Impurities, % area | | | |
|---|---|---|---|---|
| Example | 0 days | 3 days | 7 days | 14 days |
| E, vial | 0.73 | 0.96 | 1.15 | N/A |
| F, vial | 0.81 | 1.07 | 1.15 | N/A |
| G, vial | 0.67 | 0.97 | 1.05 s | N/A |
| H, vial | 0.73 | 0.99 | 1.10 | N/A |
| I, vial | 0.79 | 1.50 | 1.82 | N/A |
| E, GALAXY container | 0.74 | 0.90 | 1.02 | 1.26 |
| F, GALAXY container | 0.75 | 0.91 | 1.03 | 1.25 |
| G, GALAXY container | 0.74 | 0.94 | 1.09 | 1.38 |
| H, GALAXY container | 0.75 | 0.92 | 1.08 | 1.29 |
| I, GALAXY container | 0.85 | 1.48 | 1.95 | 2.64 |

This example demonstrates that the pharmaceutical compositions suitable for parenteral administration comprising micafungin according to the invention are significantly more stable when buffers comprising citrate and/or acetate are used, particularly relative to comparable compositions comprising ascorbic acid buffers.

Example 6: Impurity Formation in Concentrate & Ready-to-Use Compositions

Impurity formation was analyzed in both concentrate and ready-to-use aqueous pharmaceutical compositions suitable for parenteral administration comprising micafungin according to the invention by the high-performance liquid chromatography method described in Example 1. Specifically, the impurities that formed in Example Compositions J and K comprising 10 mg/mL micafungin sodium in 0.9% (w/v) saline and buffered with 25 mM citrate buffer and 100 mM citrate buffer, respectively, and in Example Composition L comprising 1.0 mg/mL micafungin sodium in 0.9% (w/v) saline and buffered with 10 mM citrate buffer, were measured. Example Compositions J and K were conditioned in vials. Example Composition L was conditioned (and tested separately) in both a vial and a GALAXY container. The formulations for Example Compositions J, K, and L are provided in Table X, below.

TABLE X

| Component | Example J | Example K | Example L |
|---|---|---|---|
| Active Agent | 10 mg/mL micafungin sodium | 10 mg/mL micafungin sodium | 1.0 mg/mL micafungin sodium |
| Buffer | 25 mM citrate | 100 mM citrate | 10 mM citrate |
| pH | 4.8 | 4.82 | 4.81 (GALAXY) 4.83 (vial) |
| Tonicity adjusting agent | 9 mg/mL saline | 9 mg/mL saline | 9 mg/mL saline |

Example Compositions J and K were conditioned at 5° C. for 64 weeks, with samples taken at time 0, at 12 weeks, at 24 weeks, at 39 weeks, and at 64 weeks. The impurities in the concentrate samples were determined using the HPLC method described in Example 1 and are shown in Table XI, below.

TABLE XI

|  | Time 0 (total impurities, % area) | 12 Weeks (total impurities, % area) | 24 Weeks (total impurities, % area) | 39 Weeks (total impurities, % area) | 64 Weeks (total impurities, % area) |
| --- | --- | --- | --- | --- | --- |
| Composition J | 0.39 | 0.50 | 0.56 | 0.64 | 0.71 |
| Composition K | 0.38 | 0.54 | 0.60 | 0.65 | 0.73 |

Example Composition L was packaged in both a GALAXY container and a vial, frozen overnight (−20° C.), and then conditioned at 5° C. for 48 weeks, with samples taken at time 0, 14 weeks, 24 weeks, 36 weeks, and 48 weeks. The impurities in the samples were determined using the HPLC method described in Example 1 and are shown in Table XII, below.

TABLE XII

|  | Time 0 (total impurities, % area) | 14 Weeks (total impurities, % area) | 24 Weeks (total impurities, % area) | 36 Weeks (total impurities, % area) | 48 Weeks (total impurities, % area) |
| --- | --- | --- | --- | --- | --- |
| Composition L (GALAXY) | 0.33 | 0.47 | 0.46 | 0.62 | 0.68 |
| Composition L (vial) | 0.31 | 0.48 | 0.47 | 0.64 | Not Tested |

As can be seen by Tables XI and XII above, concentrate and ready-to-use samples contained less than 1.0% area total impurities after being stored at 5° C. for 64 weeks and 48 weeks, respectively.

Example Compositions J, K, and L were also conditioned at 25° C. for 4 weeks, with samples taken at time 0 and at 4 weeks. The impurities in the samples were determined using the HPLC method described in Example 1 and are shown in Table XIII, below.

TABLE XIII

|  | Time 0 (total impurities, % area) | 4 Weeks (total impurities, % area) |
| --- | --- | --- |
| Composition J | 0.39 | 0.96 |
| Composition K | 0.38 | 0.98 |
| Composition L (GALAXY) | 0.33 | 1.02 |
| Composition L (vial) | 0.31 | 1.01 |

As can be seen by Table XIII above, both concentrate and ready-to-use samples contained less than about 1.0% area total impurities after being stored for 4 weeks at 25° C.

Example Composition L (packaged in both a GALAXY container and a glass vial) was also conditioned at −20° C. for 48 weeks, with samples taken at time 0, at 14 weeks, at 24 weeks, at 36 weeks, and at 48 weeks. Samples were stored at −20° C. until each time point, at which point they were thawed and the impurities were determined using the HPLC method described in Example 1, as shown in Table XIV, below.

TABLE XIV

|  | Time 0 (total impurities, % area) | 14 Weeks (total impurities, % area) | 24 Weeks (total impurities, % area) | 36 Weeks (total impurities, % area) | 48 Weeks (total impurities, % area) |
| --- | --- | --- | --- | --- | --- |
| Composition L (GALAXY) | 0.33 | 0.43 | 0.37 | 0.48 | 0.47 |
| Composition L (vial) | 0.31 | 0.41 | 0.36 | 0.45 | Not Tested |

As can be seen by Table XIV above, the ready-to-use samples contained less than 0.5% area total impurities after being stored for 48 weeks at −20° C.

As can be seen by the data presented in Tables XI through XIV, above, the stability of the concentrate Example Compositions J and K was comparable to the stability of Example Composition L in both the vial and GALAXY container.

This example demonstrates the enhanced stability of both concentrate and ready-to-use pharmaceutical compositions suitable for parenteral administration comprising micafungin according to the invention.

Example 7: Low Buffer Stability Study

Changes in pH were measured over time for compositions comprising varied but low concentrations of citrate buffer. Six compositions comprising 1.0 mg/mL micafungin sodium and 9 mg/ml saline were prepared and filled into glass vials (filled to 10 mL) at a pH value between 4.80 and 4.84. The citrate buffer concentration was varied in these compositions as shown in Table XV, below.

TABLE XV

| Example | Conc [mM] |
|---------|-----------|
| M | 0 |
| N | 0.1 |
| O | 0.2 |
| P | 0.3 |
| Q | 0.4 |
| R | 0.5 |

Example Compositions M, N, O, P, Q, and R were conditioned at ambient room temperature for 9 days, with pH measurements made at time 0, at 2 days, and at 9 days. The pH values for these compositions are shown in Table XVI, below.

TABLE XVI

| | Time 0 (pH) | 2 Days (pH) | 9 Days (pH) |
|---|---|---|---|
| Composition M | 4.80 | 6.56 | 6.81 |
| Composition N | 4.82 | 5.48 | 5.81 |
| Composition O | 4.82 | 5.24 | 5.34 |
| Composition P | 4.82 | 5.15 | 5.22 |
| Composition Q | 4.84 | 5.05 | 5.13 |
| Composition R | 4.83 | 4.97 | 5.14 |

As can be seen by Table XVI, all compositions, with the exception of Compound M, were able to maintain the pH of the compositions within 1 pH unit over 9 days at room temperature. Furthermore, Example Composition L (1 mg/ml micafungin sodium, 10 mM citrate buffer, not shown) substantially maintained a pH of 4.83 for 4 weeks at room temperature.

This example shows a citrate buffer concentration of less than 0.1 mM is not suitable for ready-to-use micafungin compositions according to the invention. Unexpectedly and advantageously, compositions comprising between about 0.1 mM and 0.5 mM citrate buffer were able to maintain a pH suitable for parenteral administration for at least 9 days. These compositions are considered especially suitable for frozen compositions, as micafungin degradation is minimized at colder temperatures and, based on the above data, significant stability is expected after thawing of the frozen formulations. Additionally, compositions comprising higher concentrations of buffer (e.g. Composition L and other compositions having greater than 5 mM buffering agent, for example, between about 5 mM and 15 mM buffering agent) are surprisingly stable for extended amounts of time at room temperature, and are considered especially useful for long-term room temperature storage of ready-to-use formulations. Similar results have been shown for concentrate formulations comprising between about 20 mM and about 400 mM buffering agent, as shown in Example 6.

Example 8: pH Range Study

The pH range at which the compositions according to invention are most stable was studied. First, MYCAMINE® samples were prepared in accordance with the product label and stored for two days at room temperature according to the label directions. In an aseptic preparation step, the lyophilized micafungin sodium powder was reconstituted as a 10 mg/mL (50 mg vial) concentrate in a 0.9 wt % saline solution. After storage of the reconstituted product for 24 hours at 25° C., a diluted, ready-to-use formulation was prepared by further diluting the reconstituted product in a volumetric flask to provide a 1 mg/mL micafungin sample in a 100 mL container. The ready-to-use formulation was then stored for an additional 24 hours at 25° C. Two days (starting from the time of reconstitution) is the maximum amount of time permitted for MYCAMINE® to be stored under these conditions, according to the product label and as described in the background section above. After storage for two days, the diluted MYCAMINE® samples were found to contain 1.75% area total impurities.

Eight samples of 1 mg/ml micafungin sodium samples according to the invention were prepared at various pH levels using micafungin sodium and 10 mM citrate buffer. Samples prepared under a pH of 5.0 used a 9 mg/ml saline tonicity adjusting agent, while those prepared above pH 5.0 used a 50 mg/ml dextrose tonicity adjusting agent. After conditioning at room temperature for 3 weeks, the impurities were measured, as shown in Table XVII, below.

TABLE XVII

| pH | 3 weeks (total impurities, % area) |
|---|---|
| 3.6 | 2.05 |
| 4.0 | 1.37 |
| 4.4 | 1.07 |
| 4.8 | 1.02 |
| 5.2 | 1.04 |
| 6.0 | 1.35 |
| 6.4 | 1.91 |
| 6.8 | 3.50 |

From these data, the pH range that maintained a total impurities level of under 1.75%, that is, the level of impurities found from the MYCAMINE® study described above, was between about 3.8 and about 6.2, as shown in FIG. 3a.

The data in Table XVII were then fitted to a polynomial, as shown in FIG. 3b. Based on this polynomial, suitable pH ranges for compositions according to the invention were determined, as seen in Table XVIII, below. To be considered stable at 3 weeks, the samples must have no more than 5.0% area total impurities. More preferably, the samples have less than 2.0% area total impurities, or less than 1.5% area total impurities.

TABLE XVIII

| Total Impurities, % area | Lower pH Limit | Upper pH Limit |
|---|---|---|
| 5.0 | 3.0 | 7.0 |
| 2.0 | 3.6 | 6.4 |
| 1.5 | 3.8 | 6.2 |

This example demonstrates the effect the pH has on the impurity levels of pharmaceutical compositions suitable for parenteral administration comprising micafungin according to the invention. ICH limits expressly limit the amount of impurities in a pharmaceutical composition to be no more than 5%. Thus, in particular, this example demonstrates the significance of the claimed pH range of about 3.0 to about 7.0 and even more so the claimed pH ranges of about 3.6 to about 6.4 and about 3.8 to about 6.2.

What is claimed:

1. A packaged sealed container comprising an aqueous pharmaceutical composition suitable for parenteral administration, the container comprising:

an aqueous pharmaceutical composition consisting of:
(i) between 0.5 mg/ml and 2.5 mg/ml micafungin sodium;
(ii) between 1 mM and 20 mM citrate buffering agent;
(iii) between 4 mg/ml and 10 mg/ml sodium chloride; and
(iv) water,
wherein the pH of the aqueous pharmaceutical composition is between 4.0 and 5.5,
and the aqueous pharmaceutical composition is provided in the packaged sealed container,
wherein the aqueous pharmaceutical composition is sterile and ready to use without further compounding or processing, and
wherein the aqueous pharmaceutical composition has less than 1.5% area total impurities after formulation and storage thereof at room temperature for three weeks, as determined by HPLC analysis.

2. The packaged sealed container according to claim 1, wherein the aqueous pharmaceutical composition has less than 0.5% area total impurities after formulation and storage thereof at −20° C. for 48 weeks, as determined by HPLC analysis.

3. The packaged sealed container according to claim 1, wherein the aqueous pharmaceutical composition is frozen.

4. The packaged sealed container according to claim 1, wherein the sealed container comprises a vial or a syringe.

5. The packaged sealed container according to claim 1, wherein the sealed container comprises a plastic bag or a bottle.

6. The packaged sealed container according to claim 1, wherein the aqueous pharmaceutical composition consists of about 1 mg/ml of the micafungin sodium, about 10 mM of the citrate buffering agent, about 9 mg/ml of the sodium chloride, and the water.

7. The packaged sealed container according to claim 4, consisting of the vial or syringe and the aqueous pharmaceutical composition.

8. The packaged sealed container according to claim 5, consisting of the plastic bag or bottle and the aqueous pharmaceutical composition.

* * * * *